United States Patent
Mydlowec et al.

(10) Patent No.: US 6,571,226 B1
(45) Date of Patent: May 27, 2003

(54) METHOD AND APPARATUS FOR AUTOMATED DESIGN OF CHEMICAL SYNTHESIS ROUTES

(75) Inventors: William J. Mydlowec, Sunnyvale, CA (US); Jessen Yu, Sunnyvale, CA (US)

(73) Assignee: Pharmix Corporation, Redwood City, CA (US)

( * ) Notice: Subject to any disclaimer, the term of this patent is extended or adjusted under 35 U.S.C. 154(b) by 0 days.

(21) Appl. No.: 09/523,334

(22) Filed: Mar. 10, 2000

Related U.S. Application Data

(60) Provisional application No. 60/124,308, filed on Mar. 12, 1999.

(51) Int. Cl.[7] .............................................. G06F 15/18
(52) U.S. Cl. .......................................... 706/13; 706/12
(58) Field of Search ...................................... 706/13, 12

(56) References Cited

U.S. PATENT DOCUMENTS

| | | | |
|---|---|---|---|
| 5,148,513 A | | 9/1992 | Koza et al. ................... 706/13 |
| 5,343,554 A | | 8/1994 | Koza et al. ................... 706/13 |
| 5,434,796 A | * | 7/1995 | Weininger .................... 706/12 |
| 5,742,738 A | * | 4/1998 | Koza et al. ................... 706/13 |
| 5,848,403 A | | 12/1998 | Gabriner et al. .............. 706/13 |
| 5,930,780 A | | 7/1999 | Hughes et al. ................ 706/13 |

OTHER PUBLICATIONS

"Sidelobe Reduction in Array–Pattern Synthesis Using Genetic Algorithm", Keen–Keong Yan and Yilong Lu, vol. 45, No. 7, Jul. 1997, pp. 1117–1122.

Linear Array Synthesis Using a Hybrid Genetic Algorithm:, Michael J. Buckley, vol. 1, Jul. 1996, pp. 584–587.

* cited by examiner

*Primary Examiner*—George B. Davis
(74) *Attorney, Agent, or Firm*—Moser, Patterson & Sheridan, L.L.P.

(57) ABSTRACT

Method and apparatus for designing a synthesis route for a target molecule is provided. The method for designing a synthesis route for a target molecule comprises: generating a plurality of individuals, wherein each individual encodes a synthesis route; decoding each individual to produce a synthesis route comprising at least one reactant molecules and at least one reaction; and determining how well the synthesis route satisfies a design goal. A computer readable medium containing instructions for a computer program executable by the computer to perform a method for designing a synthesis route for a target molecule is also provided. The apparatus comprises a parallel computer system for executing instructions of a computer program to perform a method for designing a synthesis route for a target molecule.

38 Claims, 8 Drawing Sheets

METHOD AND APPARATUS FOR AUTOMATED DESIGN OF CHEMICAL SYNTHESIS ROUTES

This application claims the benefit of provisional application No. 60/124,308 filed Mar. 12, 1999.

BACKGROUND OF THE INVENTION

1. Field of the Invention

The invention generally relates to the automated design of chemical synthesis routes. More specifically, the invention relates to designing chemical synthesis routes using computer-implemented algorithms.

2. Background of the Related Art

Chemical synthesis is the process by which complex chemical compounds are created from simpler ones. Many important drugs and advanced materials are produced utilizing chemical synthesis.

Chemical compounds are made up of atoms of different elements, held together by chemical bonds. Synthesis usually involves breaking existing bonds and forming new bonds using chemical reactions. Synthesis of a complex molecule involves a sequence of reactions leading from the available starting materials to the desired end product. Such a reaction sequence is called a synthesis route.

The design of synthesis routes must consider many factors, such as the availability and cost of starting materials, the energy and time requirements of reactions, and the cost of purifying the end products. Creating synthesis routes is a difficult task for which there is no single design protocol. Chemists who successfully design synthesis routes require experience, intuition, and years of effort.

Genetic algorithms (GAs) are problem-solving algorithms based on the mechanics of natural selection and genetics. The motivation for GAs is the success of biological evolution in solving difficult problems in nature.

GAs operate on populations of individuals representing potential solutions to a problem. Individuals in GA usually encode solutions as fixed-length bit strings (i.e., strings of 0's and 1's). GAs solve problems by evolving successively better populations using a survival-of-the-fittest process. The fitness of an individual solution is determined by a problem-specific fitness function.

The initial population typically contains a plurality of randomly-generated bit strings. Subsequent generations of the population are produced by genetic operations that mimic recombination (crossover), mutation, and other biological operations.

Genetic programming (GP) is an extension of the Genetic Algorithm. In GP, individuals are computer programs of varying shapes and sizes. The programs are usually LISP expressions or hierarchical program trees. The fitness of a GP program is determined by first executing it, then evaluating its results using a problem-specific fitness function.

The initial population usually contains randomly-generated but syntactically-correct programs. Subsequent generations of the population are produced by biologically-inspired operations that act on subprograms and preserve syntactic correctness.

GP is widely-applicable since many problems have solutions that can be easily encoded as computer programs. GP has already been used to produce human-competitive solutions to difficult problems such as electronic circuit design.

Computer-aided chemical synthesis programs help chemists design synthesis routes. Such programs are often consulted by practicing chemists when planning syntheses of complex molecules. The general field concerning computer-aided chemical synthesis programs is typically known as Computational Chemistry and includes the field of Computer-Aided Organic Synthesis (CAOS).

The presently available solutions and most other computer-aided synthesis programs operate retrosynthetically (i.e., backwards from the target molecule to the starting material). The program user supplies the target molecule, and then the programs output a series of possible precursor molecules for forming the target molecule. Repeating this process results in the growth of a tree of possible routes, leading from the target back to more accessible starting materials.

Some of the presently available synthesis techniques do not automatically generate synthesis routes. Rather, they are interactive with the user, only helping guide the selection of promising routes. Other techniques can be used to generate retrosynthetic routes without human interaction, but often produce backwards transformations that do not correspond to real chemical reactions. Further, all of the previously developed programs depend on empirical databases, data tables, reaction matrices, etc., listing all possible synthetic transformations. This limits their predictions to known transformations stored in their databases. In one example of the use of genetic algorithms in chemistry, U.S. Pat. No. 5,434,796 describes an encoding technique that allows cyclical chemical graphs to be represented by bit strings in a genetic algorithm.

All of the above methods evolve molecules only, and they do not address the problem of how to create synthesis routes for evolved molecules. Presently, there is no successful application of genetic algorithms or genetic programming to the problem of inventing chemical synthesis routes. Therefore, there is a need for a method and apparatus for the automated design of chemical synthesis routes utilizing genetic algorithms and/or genetic programming for inventing chemical synthesis routes that satisfy prespecified design goals.

SUMMARY OF THE INVENTION

The present invention provides a method and apparatus for the automated design of chemical synthesis routes that satisfy prespecified design goals. More specifically, the present invention includes a method and apparatus for running an iterative process applied to a population of individuals that encode chemical synthesis routes.

The present invention includes a method for determining the outcome of a chemical reaction, a method for determining the structural similarity of two molecules, and a method for evaluating the properties of a chemical synthesis route.

The method for designing a synthesis route for a target molecule comprises: generating a plurality of individuals, wherein each individual encodes a synthesis route; decoding each individual to produce a synthesis route comprising at least one reactant molecule and at least one reaction; and determining whether the synthesis route satisfies a design goal.

The invention also provides a computer readable medium containing instructions for a computer program executable by the computer to perform a method for designing a synthesis route for a target molecule.

Another aspect of the invention provides an apparatus comprising a parallel computer system for executing instructions of a computer program to perform a method for designing a synthesis route for a target molecule.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Overview

The present invention provides a method and apparatus for designing chemical synthesis routes that satisfy prespecified design goals. The chemical synthesis routes of the present invention are sequences of chemical reactions that transform available starting molecules into a desired final product molecule.

In one embodiment of the present invention, a user specifies one or more goals for a chemical synthesis route that is to be designed. The design goals include a description of a target molecule which the synthesis route should produce as a final product. Additional design goals may include, for example, minimizing the number of reactions, maximizing the yield of the final product, minimizing the overall cost, and so on. In general, a combination of many design goals may be specified. The automated design process of the present invention generates a complete synthesis route that satisfies the specified design goals. The generated synthesis route is then presented to the user.

Figure 1:
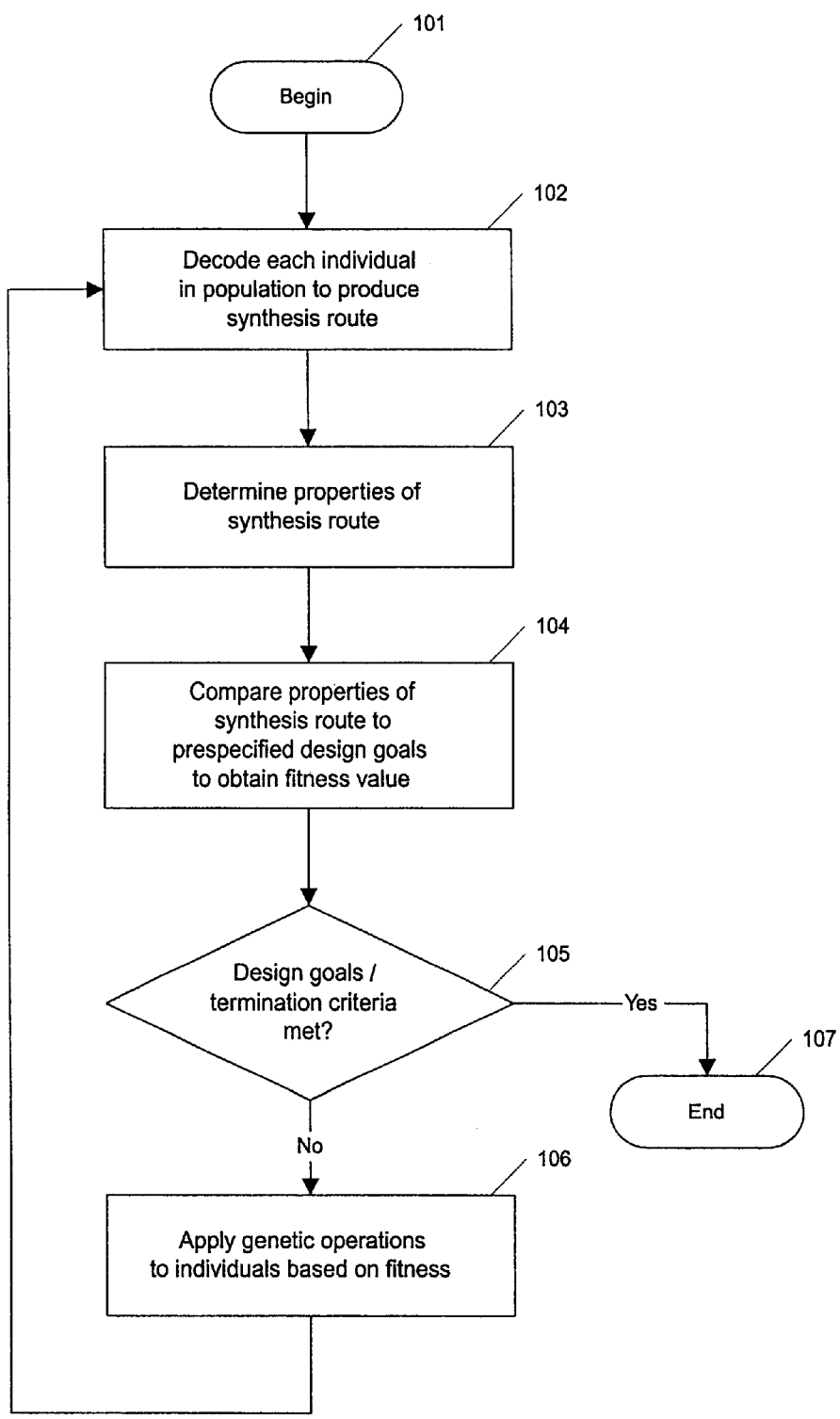
FIG. 1 is a flow diagram illustrating a method for designing chemical synthesis routes that satisfy prespecified design goals.

FIG. 1 is a flow diagram illustrating a method for designing chemical synthesis routes that satisfy prespecified design goals. The process as shown in FIG. 1 is applied to a population of individuals that encode chemical synthesis routes. The population may be created in a variety of ways (for example, randomly) or may be supplied to begin the process (101).

Using the population of individuals, the process decodes each individual in the population to produce a synthesis route (102). Next, the properties of each developed synthesis route are determined (103). Once the properties are determined, they are compared to the prespecified design goals to obtain a fitness value (104).

A test then determines if the design goals or termination criteria have been met (105). If they have, the process ends (107). If they have not, genetic operations are applied to the individuals in the population to continue the evolutionary process (106). After applying the genetic operations, a new population of individuals is provided, and the process returns to (102) to repeat the steps for the new population of individuals. The steps (102) to (106) are repeated until a synthesis route for an individual satisfies the design goals.

Chemical Synthesis Routes

Figure 2:
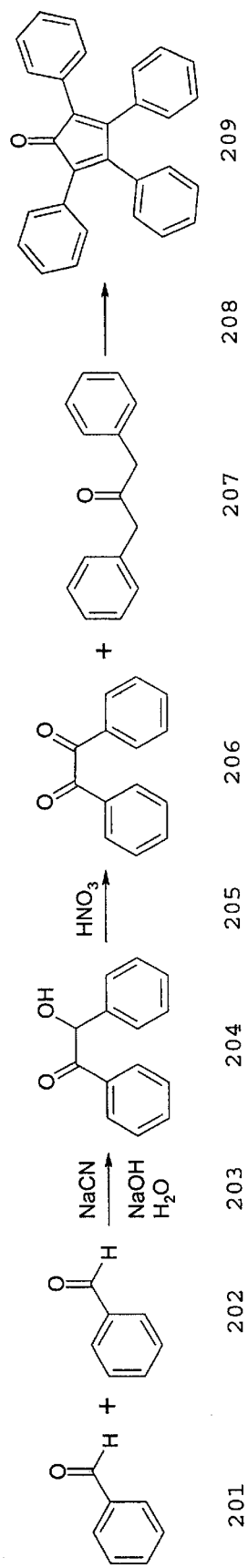
FIG. 2 is a sequential diagram illustrating an example of an individual of the population encoding a chemical synthesis route.

The chemical synthesis routes of the present invention comprise a sequence of chemical reactions that transform available starting molecules into desired products molecules. FIG. 2 is a sequential diagram illustrating an example of an individual of the population encoding a chemical synthesis route. The synthesis routes of the present invention are hierarchical in form; however, we still describe the synthesis routes as reaction "sequences." FIG. 3 is a hierarchical diagram illustrating the hierarchical structure of the synthesis route of FIG. 2.

Figure 3:
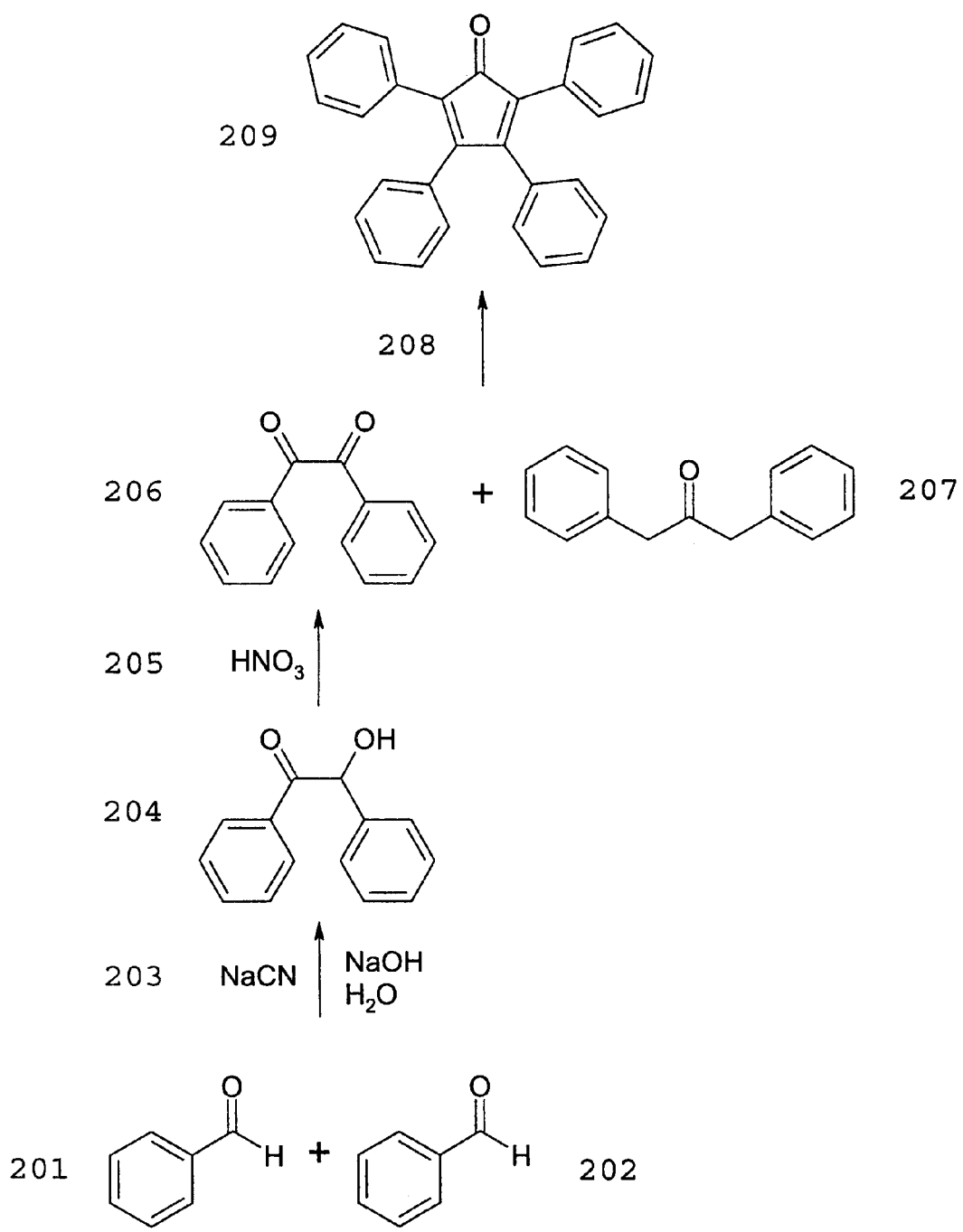
FIG. 3 is a hierarchical diagram illustrating the hierarchical structure of the synthesis route of FIG. 2.

Referring to FIGS. 2 and 3, the exemplar synthesis route as shown has three reactions. First, reaction (203) combines molecules (201) and (202) into molecule (204). Second, reaction (205) transforms molecule (204) into molecule (206). Third, reaction (208) combines molecules (206) and (207) into molecule (209). Molecules (201), (202), and (207) are starting materials, molecules (204) and (206) are intermediates, and molecule (209) is the final product.

Encoding Synthesis Routes as Lisp Expressions

One embodiment of the present invention applies genetic programming (GP) to design of chemical synthesis routes by encoding synthesis routes as Lisp expressions (programs). In general, any encoding may be used so long it preserves the hierarchical structure of the synthesis route.

In one embodiment of the present invention, the Lisp expressions comprise functions (instructions) which are evaluated (executed) to build a synthesis route. Each expression evaluation starts with a blank synthesis route. As functions in that expression are evaluated, they add reactant molecules and reactions to the synthesis route.

The following Lisp expression, when evaluated (executed), constructs the synthesis route shown in FIGS. 2 and 3. Standard Lisp-style depth-first evaluation is used:

```
(REACTION
    (REACTION
        (REACTION
            (MOLECULE 3242)
            (MOLECULE 3242)
            (CONDITIONS 215)
            1
        )
        (CONDITIONS 650)
        0
    )
    (MOLECULE 3194)
    (CONDITIONS 408)
    2
)
```

Figure 4:
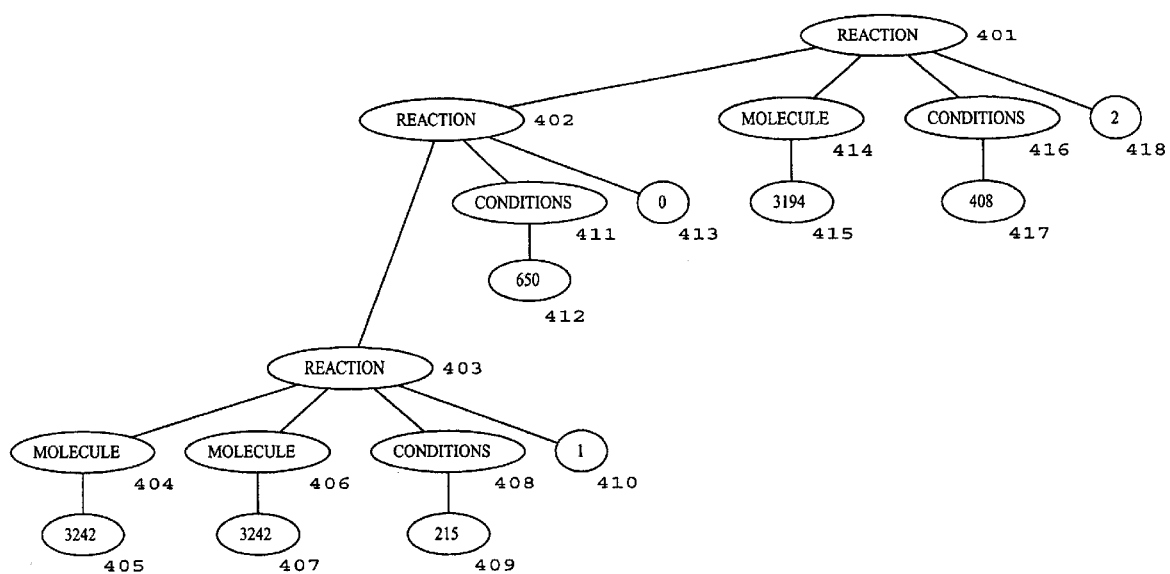
FIG. 4 is a hierarchical diagram illustrating the exemplar Lisp program having tree-like structure.

FIG. 4 is a hierarchical diagram illustrating the exemplar Lisp program having tree-like structure. FIG. 4 represents a program tree of the above Lisp expressions, corresponding to the synthesis routes shown in FIGS. 2 and 3.

MOLECULE Function and Molecule Database

The MOLECULE function accesses a database of available starting materials. The database (or data structure) may vary in contents and size depending on specific applications. For example, the database may comprise reagents that are available for purchase from chemical manufacturers, or may be selected based on certain problem-specific criteria. In one embodiment of the present invention, the Acros Organics database of approximately 10,000 chemicals is used.

The MOLECULE function takes one argument, an integer representing a record index in the molecule database (modulo if out-of-range). The MOLECULE function retrieves the specified record, adds the molecule from the record to the synthesis-route-under-construction, and returns the molecule to the calling function.

For example, in FIG. 4, the MOLECULE function (404) retrieves record 3242 from the molecule database as specified by the integer constant (405). The MOLECULE function (404) then adds the molecule from record 3242 to the synthesis-route-under-construction, corresponding to the molecule (201) in FIGS. 2 and 3. Then, the MOLECULE function (404) returns the retrieved molecule to the calling function (403).

CONDITIONS Function and Reaction Database

The CONDITIONS function accesses reaction conditions from a database of known chemical reactions conditions. The conditions typically include temperature, solvents, reagents, and other factors required for a reaction to occur. In the present embodiment, a proprietary database of approximately 6,000 example reactions from organic chemistry literature is used. In alternative embodiments, other databases having different number of entries or different data arrangements can be used to provide reaction conditions.

The CONDITIONS function takes one argument, an integer representing a record index in the reaction database (modulo if out-of-range). The CONDITIONS function retrieves the specified record, adds the set of conditions contained in the record to the synthesis-route-under-construction, and returns the set of conditions contained in the record to the calling function.

For example, in FIG. 4, the CONDITIONS function (408) retrieves record 215 from the reaction database as specified by the integer constant (409) and adds the set of conditions contained in record 215 to the synthesis-route-under-construction. Then the CONDITIONS function returns the set of conditions contained in record 215 to the calling function (403).

REACTION Function and CAMEO Reaction Predictor

The REACTION function simulates a chemical reaction using a reaction prediction mechanism. In the preferred mode of the present invention, a computer-based chemical reaction predictor is used. Note that alternative approaches are possible, for example, physically performing the reaction in a laboratory and observing the result. In one embodiment, the present invention uses a modified version of the CAMEO (i.e., Computer Assisted Mechanistic Evaluation of Organic Reactions) program developed by Jorgensen and others and distributed by LHASA UK. The CAMEO program is described by Jorgensen, William L., Laird, Ellen R., Gushurst, Alan J., Fleischer, Jan M, Gothe, Scott A., Helson, Harold E., Paderes, Genevieve D., and Sinclair, Shenna, in 1990, in CAMEO: a program for the logical prediction of the products of organic reactions. *Pure and Applied Chemistry*, Volume 62, Number 10, Pages 1921–1932, which is hereby incorporated by reference in its entirety.

The modified CAMEO program assesses the feasibility of individual reaction steps and works in the synthetic (forward) direction. The user inputs reactant molecules and reaction conditions, and then the modified CAMEO predicts the resulting product molecules. Rather than relying on reaction databases, the modified CAMEO uses expert system rules to predict reactions in several major classes. The advantage of the rule-based approach is that the modified CAMEO can predict novel reactions that are mechanistically reasonable. The modified CAMEO is capable of predicting reactions in many major classes, including: Basic/Nucleophilic, Acidic/Electrophilic, Electrophilic Aromatic Substitution (EAS), Radical, Heterocyclic, Pericyclic, Oxidative/Reductive, Carbene, Pd Organometallic and Photochemical.

The CAMEO program was extensively modified so that the program could be invoked as a subroutine in the process of the present invention. Numerous error handlers were added to trap the variety of cases where it rejects its inputs, runs out of memory, exceeds a prespecified amount of computer time, or crashes.

The REACTION function takes as arguments: one or more reactant molecules, one set of reaction conditions, and one integer used for selecting among multiple product molecules. The REACTION function submits the substrate molecules and conditions to the modified CAMEO program, which processes this input and returns a list of possible product molecules, ranked according to likelihood of occurrence. The REACTION function uses its integer argument to select the CAMEO product molecule with the corresponding rank (modulo if out-of-range). Then REACTION function adds a reaction arrow and the selected product molecule to the synthesis-route-under-construction, and returns the selected product molecule to another calling function, if any.

For example, in FIG. 4, the REACTION function (403) simulates a reaction involving reactant molecules returned from the MOLECULE functions (405) and (407) with the conditions returned from the CONDITIONS function (408). The modified CAMEO program processes this data and returns a list of possible product molecules. The REACTION function selects the product molecule at list position 1 as specified by the integer constant (410). Then the REACTION function adds a reaction arrow and the selected product molecule to the synthesis-route-under-construction, corresponding to arrow (203) and molecule (204) in FIGS. 2 and 3. Next, the REACTION function returns the selected product molecule (204) to the calling function (402).

To continue with the example as shown in FIG. 4, the calling function (402), also a REACTION function, simulates a reaction involving the selected product molecule from REACTION function (403) with the conditions returned from the CONDITIONS function (411) for record 650 as specified by integer constant (412). The modified CAMEO program processes this data and returns a list of possible product molecules. The REACTION function (402) selects the product molecule at list position 0 as specified by the integer constant (413). Then the REACTION function adds a reaction arrow and the selected product molecule to the synthesis-route-under-construction, corresponding to arrow (205) and molecule (206) in FIGS. 2 and 3. Next, the REACTION function returns the selected product molecule (206) to the calling function (401).

The calling function (401), also a REACTION function, simulates a reaction involving the selected product molecule from REACTION function (402) and reactant molecules returned from the MOLECULE function (414) for record 3194 as specified by integer (415) with the conditions returned from the CONDITIONS function (416) for record 408 as specified by integer constant (417). The modified CAMEO program processes this data and returns a list of possible product molecules. The REACTION function (401) selects the product molecule at list position 2 as specified by the integer constant (418). Then the REACTION function (401) adds a final product molecule to the synthesis-route-under-construction, corresponding to arrow (208) and molecule (209) in FIGS. 2 and 3.

If no reaction occurs for a given set of substrate molecules and conditions, the modified CAMEO program does not return any predicted product molecules. However, the REACTION function must still return a value so that synthesis route construction may continue. In these cases, the REACTION function uses the integer argument to select one of the reactant molecule arguments as a return value and removes from the synthesis-route-under-construction the non-selected reactant molecules, as well as everything that precedes them in the synthesis. Optionally, the program tree can be modified to reflect the deletion in the synthesis route.

Similarly, if one of the reactant molecules submitted to the modified CAMEO program does not actually participate in the resulting reaction mechanism, the REACTION function removes from the synthesis-route-under-construction the non-participating reactant molecules, as well as everything that precedes them in the synthesis. Optionally, the program tree can be modified to reflect the deletion in the synthesis route.

Other Functions for Chemical Synthesis

In general, functions may include any function which modifies a synthesis-route-under-construction. For example, there could be a function named CHROMO which adds a chromatography separation step to the synthesis-route-under-construction. The invention contemplates utilizing a variety of functions to construct a synthesis route.

Constrained Program Structure

In one embodiment, program trees conform to a constrained structure. The constraints ensure that the root function in the program tree is a REACTION function. The constraints also ensure that every function receives argument values of the required types (as described above for each function). Alternatively, program trees may not conform to the particular structure shown in FIG. 4 or any constrained structure.

Input Parameters

The process of the present invention requires several input parameters. The input parameters for the present embodiment are given here, but it should be noted that other values could also be used.

The main input parameter is the target molecule for which a synthesis route is to be designed. Another input parameter is the population size. The population size parameter (M) determines how many individuals will be created, evaluated, and reproduced during each generation. In the present embodiment, a population size of 10,000 is used.

Other parameters establish resource limits for individuals. In the present embodiment, a maximum program tree size of 500 functions is used. Also, an upper limit of 10 seconds of computer time per individual evaluation (including chemical database queries, reaction predictions, and fitness evaluation) is enforced.

Another set of parameters establish probabilities of selecting each genetic operation (discussed below). In the present embodiment, the probabilities are: 60% crossover ($P_{crossover}$), 20% molecule noise ($P_{mol\_noise}$), 10% mutation ($P_{mutation}$), and 10% copy ($P_{copy}$).

Population Creation

Figure 5A:
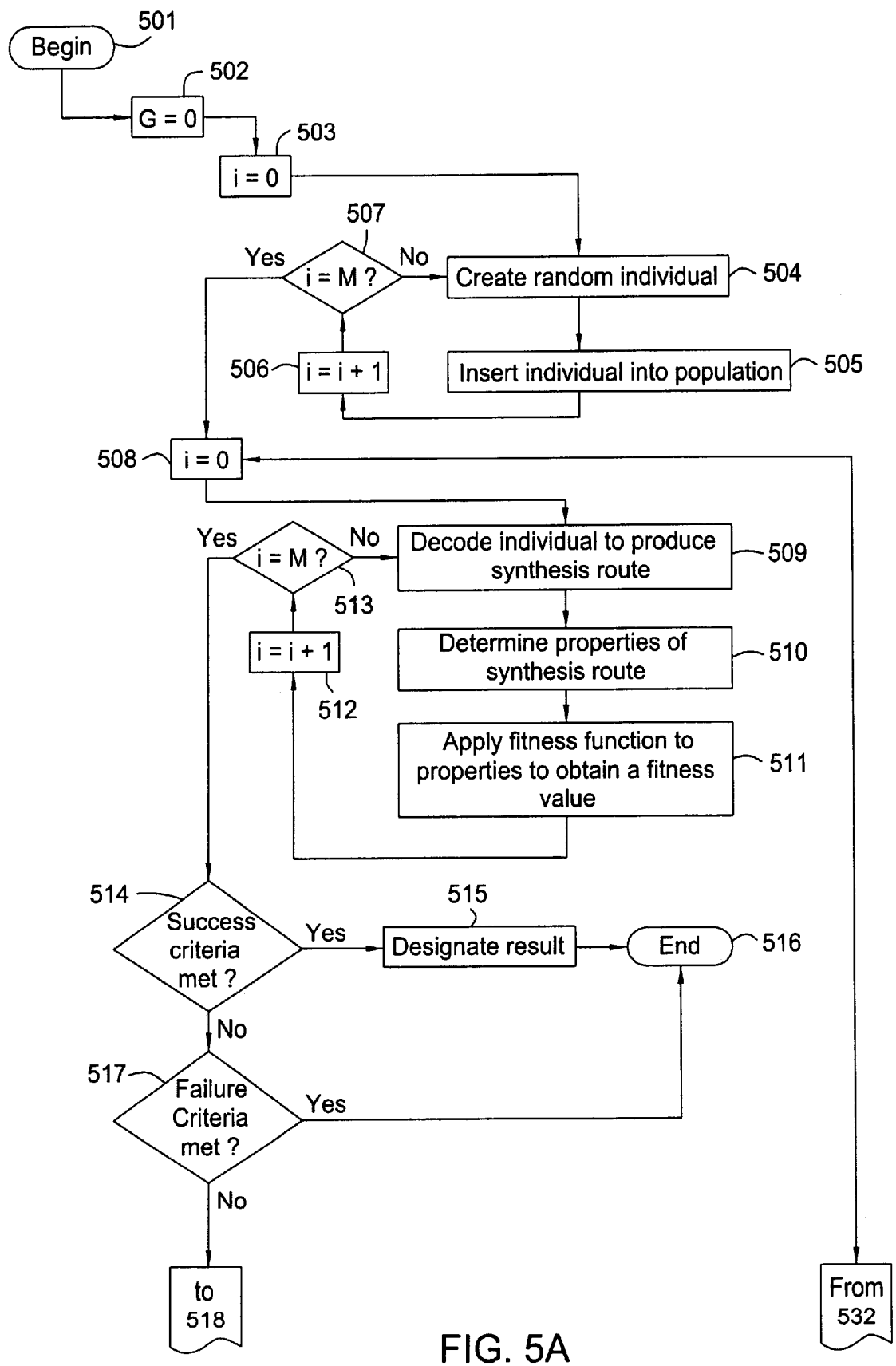
FIGS. 5A and 5B are flow diagrams illustrating the process of the present invention for designing chemical synthesis routes that satisfy prespecified design goals.
Figure 5B:
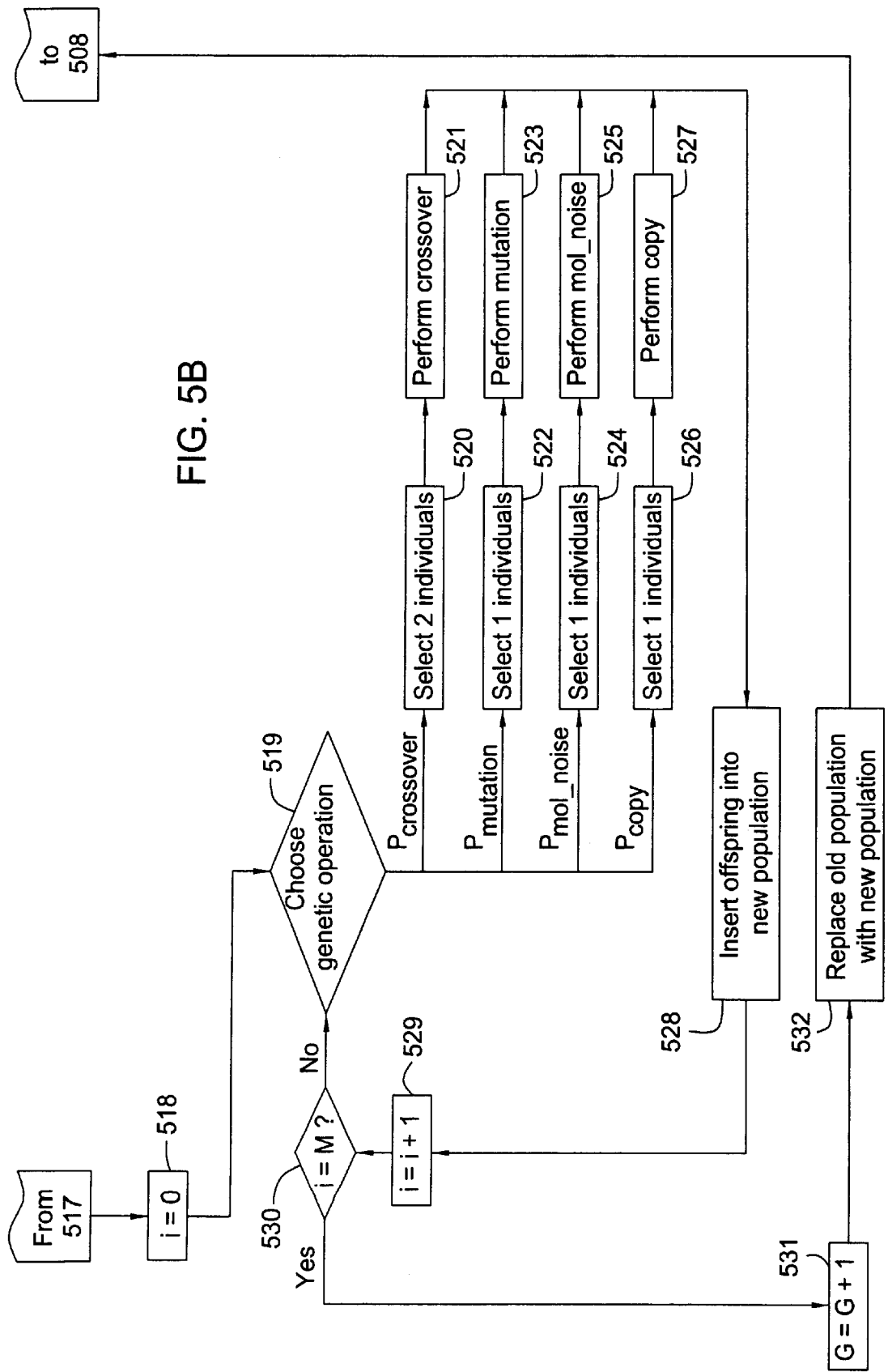

FIG. 5 is a flow diagram illustrating the process of the present invention for designing chemical synthesis routes that satisfy prespecified design goals. The process of the present invention begins by creating an initial population of individuals as shown in FIG. 5. In one embodiment, the individuals in the initial population are randomly generated. In one embodiment, the initial population is randomly generated utilizing a "ramped half-and-half" method that is well known in the art. Other methods of creating the initial population, such as using previous solutions, approximate solutions, and other databases or data structures containing individuals encoding synthesis routes, can also be utilized for generating the initial population.

The first step in population creation at (502) is to initialize the generation number (G) to 0. Next at (503), a count of individuals (i) is also initialized to 0. At (504), an individual is randomly generated. Then at (505), the randomly generated individual is inserted into the initial population.

Then at (506), the count of individuals is incremented. A test at (507) determines whether the initial population has been completely generated. If the count of individuals (i) is less than the population size (M), the process returns to (504) to create another individual. Otherwise, the population creation is complete and the process advances to fitness evaluation at (508).

Fitness Evaluation

The process of the present invention involves evaluating the fitness of the individuals in the population as shown in FIG. 5. After population creation ends at (507), or after performing genetic operations is completed at (530) (discussed below), fitness evaluation occurs.

The first step in fitness evaluation at (508) is to initialize a count of individuals (i) to 0. Next at (509), the ith individual is evaluated to produce a chemical synthesis route. During this evaluation, the chemical and reaction databases will be queried and the chemical reaction predictor will be invoked (as described above).

Next, at (510), the properties of the produced synthesis route are determined. These properties include a measure of structural similarity between the final product molecule for the synthesis route and the prespecified target molecule (discussed below). Other properties of the synthesis route may also be determined, for example, a yield estimate of the final product or a cost estimate for the entire synthesis.

Next, at (511), a fitness value for the ith individual is obtained. The fitness value incorporates the properties of the synthesis route in a way that allows two individuals to be compared to see which better achieves all of the design goals (discussed below). If an error is encountered while evaluating an individual, particularly when running the chemical reaction predictor, the error is trapped and the individual is assigned a worst fitness value. The fitness evaluation continues to the next individual. The case where an individual evaluation exceeds a prespecified time limit is handled similarly.

At (512), the count of individuals is incremented. A test at (513) determines whether the fitness evaluation has been completed for all individuals of the population. If the count of individuals (i) is less than the population size (M), the process returns to (509). Otherwise, the fitness evaluation is complete, and the process advances to testing termination criteria at (514).

Molecule Similarity

One measure of structural similarity between two chemicals is the size of the maximum common subgraph (MCS) of the two chemicals. A graph isomorphism algorithm such as Ullmann's can be used to calculate the MCS. Unfortunately, finding MCS is a computationally-intensive problem which is known to be NP-complete. In the preferred embodiment of the present invention, an approximate measure of structural similarity based on molecule fingerprints is used. Fingerprints are bit strings that abstractly represent certain structural features of a molecule. Fingerprints do not encode specific predefined molecular substructures, and there is no specific meaning to fingerprint features.

A fingerprint-generating algorithm examines the molecule and generates a pattern for each path of atoms and bonds up to some fixed length. For example, the molecule OC=CN would generate the following patterns:

| 0-bond paths: | C    | O    | N  |
|---------------|------|------|----|
| 1-bond paths: | OC   | C=C  | CN |
| 2-bond paths: | OC=C | C=CN |    |
| 3-bond paths: | OC=CN |     |    |

Each pattern can be mapped to a unique number, which is then used as the seed for a pseudo-random number generator (RNG). The pseudo-RNG outputs a set of bits (typically 4 or 5 per pattern) which is added (with a logical OR) to the fingerprint. Because each set of bits is produced by a pseudo-RNG, the sets will likely overlap. Therefore, a fingerprint can indicate if a certain pattern is absent in a molecule with 100% certainty, but can only indicate if a pattern is present with some probability.

Fingerprints can be quickly compared using a distance metric to produce an approximate measure of structural similarity. In the present embodiment, the Tanamoto coefficient is used a distance metric. The Tanamoto coefficient between two fingerprints A and B is simply the number of bits in A∩B divided by the number of bits in A∪B. Therefore, the Tanamoto coefficient is always a number between 0 and 1, where higher numbers indicate more similarity. Alternatively, other distances and metrics may be used.

Fitness Function

Each individual is assigned a fitness value that incorporates the properties of its synthesis route in a way that allows two individuals to be compared to see which better achieves all of the design goals.

In one embodiment of the present invention, the Tanamoto coefficient is utilized as a fitness value. Therefore, the fitness value can range from 0 to 1, where higher numbers indicate more similarity between final product and target molecule. In the case where the final product exactly matches the target molecule, the fitness value will equal 1.0.

In other embodiments, the fitness value can incorporate other design goals. For example, another design goal might be to maximize yield of the final product. In this case, the yield value ranges from 0 (0%) to 1 (100%). One way to incorporate yield into the fitness value is to simply add the yield value to the Tanamoto coefficient. Thus, the fitness value would range from 0.0 to 2.0, where higher numbers indicate better achievement of design goals.

In general, any number of design goals can be integrated into a fitness value. Also, other fitness rankings can be utilized, including character designations and other combinations of rankings and values.

Termination Criteria

The process of the present invention involves testing if the termination criteria for the run have been met as shown in FIG. 5. After population fitness evaluation ends at (513), termination criteria are tested.

At (514) the success criteria are tested. The success criteria are usually related to the fitness value of the best-so-far individual. In one embodiment, the success criterion is an individual in the population whose synthesis route produces the target molecule as the final product.

The test at (514) terminates the process of the current invention if the success criteria have been met. In that case, at (515) the result of the run is designated to be the synthesis route produced by the individual with the best-so-far fitness value, and the process ends at (516).

If the success criteria have not been met, the failure criteria are tested at (517). The failure criteria are usually related to an upper bound on computer time. In one embodiment, the failure criterion is performance of 500 generations without satisfying the success criteria. Alternatively, other failure criteria can be used.

The test at (517) terminates the process of the current invention if the failure criteria have been met. Otherwise, the process advances to performing genetic operations at (518), which generates a new population of individuals.

Genetic Operations

The process of the present invention involves performing genetic operations on the individuals in the population to produce a new generation as shown in FIG. 5. After termination criteria are tested, genetic operations are performed.

The first step at (518) initializes a count of individuals (i) to 0. Next at (519), a genetic operator is selected The possible genetic operations of crossover, mutation, and copy are each assigned a probability of being selected ($P_{crossover}$, $P_{mutation}$, $P_{mol\_noise}$, and $P_{copy}$ respectively), such that the sum of the probabilities of one. A genetic operation is probabilistically selected.

Next there is a selection step (520, 522, 524, or, 526) for one or more individuals to be used for the genetic operation. This selection step probabilistically selects a parent individual from the population, such that individuals having relatively high fitness values are preferred over individuals having relatively low fitness values. The genetic operation of crossover requires selection of a second parent individual also based on fitness.

Next the selected genetic operation is performed on the parent individual or individuals:

If crossover was selected, then the crossover operation is performed at (521), producing one offspring individual. The offspring's program tree is created by copying the program tree of the first parent, deleting a randomly-selected subtree, then inserting in its place a randomly-selected subtree from the program tree of second parent. The crossover operation produces a program tree that obeys the constrained program structure of the present invention (discussed above).

If mutation was selected, then the mutation operation is performed at (523), producing one offspring individual. The offspring's program tree is created by copying the program tree of the first parent, deleting a randomly-selected subtree, then inserting in its place a randomly-generated subtree. The mutation operation produces a program tree that obeys the constrained program structure of the present invention (discussed above).

If molecule noise was selected, then the non-standard molecule noise operation is performed at (525), producing one offspring individual. The offspring's program tree is created by copying the program tree of the first parent, then performing the molecule noise operation (as described below). The molecule noise operation produces a program tree that obeys the constrained program structure of the present invention (discussed above).

If copy was selected, then the copy operation is performed at (527), producing one offspring identical to the selected individual.

At (528), the offspring individual is inserted (added) into the new population.

At (529), the count of individuals is incremented. A test at (530) determines whether the new population has been completely generated. If the count of individuals (i) is less than the population size (M), the process returns to (519). Otherwise, the genetic operations are complete, and a new generation of individuals has been created. At (531), the generation number (G) is incremented. At (532), the old population is replaced with the new population. Then the process returns to fitness evaluation at (508) to evaluate each individual of the new population.

Molecule Noise Operation

The process of the present invention includes a non-standard genetic operation called molecule noise (525) that operates on the integer argument of the MOLECULE function. Recall that the MOLECULE function accesses a database of available starting materials, returning the molecule from the database whose record index is specified by the integer argument.

The molecule noise operation first selects a random MOLECULE function from the individual. It then evaluates the selected MOLECULE function to get the existing database molecule. Next, a desired molecule similarity is randomly generated using noise between −1.0 and 1.0, such that: desired similarity=1.0 − absolute value of noise. Then, the molecule database is searched to find a new molecule whose similarity to the existing molecule is closest to the desired similarity. All such molecule comparisons are done using molecule fingerprints and distance metrics (as described above). Finally, the integer argument of the MOLECULE function is reset to be the database record index of the newly-selected molecule.

In the preferred embodiment of the present invention, gaussian noise with mean of 0.0 and standard deviation of 0.05 is used. Other embodiments may use other types of noise.

As an example applied to an individual selected for molecule noise operation, a desired similarity value is generated and one molecule encoded by the selected individual is selected. A new individual is produced by modifying the selected individual to encode a new molecule, such that the new molecule has the desired similarity to selected molecule.

Parallel Computer System

Parallel processing is advantageous for implementation of the present invention because of the uncoupled nature of the time-consuming fitness evaluations. Parallelization can be used with almost one-hundred percent efficiency by the process of the present invention.

Figure 6:
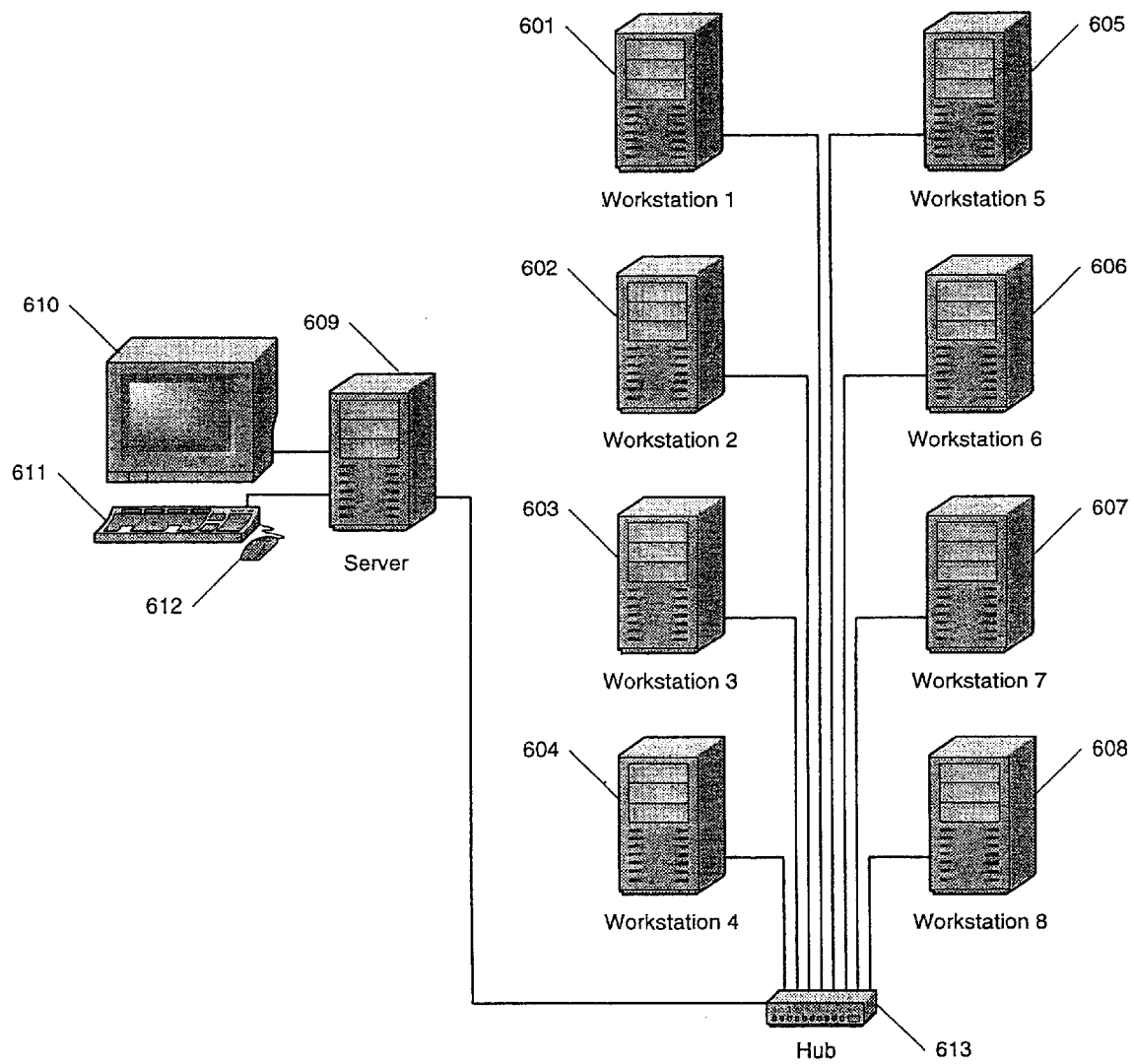
FIG. 6 is a schematic diagram showing the hardware of a parallel computer system of the invention.

FIG. 6 is a schematic diagram showing the hardware of a parallel computer system of the invention. In one embodiment, the process of the present invention is run on a Beowulf-style parallel computer as shown in FIG. 6. The hardware comprises 8 Intel Pentium II workstations which are diskless and headless (601–608), and an additional Intel Pentium II server with a hard disk (609), a video display (610), a keyboard (611), and a mouse (612). Each computer is connected to the 100BaseT Ethernet network via a hub (613).

Each of the 8 workstations (601–608) runs a minimal version of the Linux operating system, while the server (609) runs a full version of Linux with including DHCP, tFTP, and NFS daemons (programs). When the system boots, the 8 diskless workstations (601–608) use DHCP requests to find the server (609), use tFTP to download their Linux kernels into RAM, and use NFS to read shared files from the server hard disk. Although specific hardware and software have been described for this embodiment, it is understood that the invention can be applied utilizing a variety of other compatible hardware and software.

Figure 7:
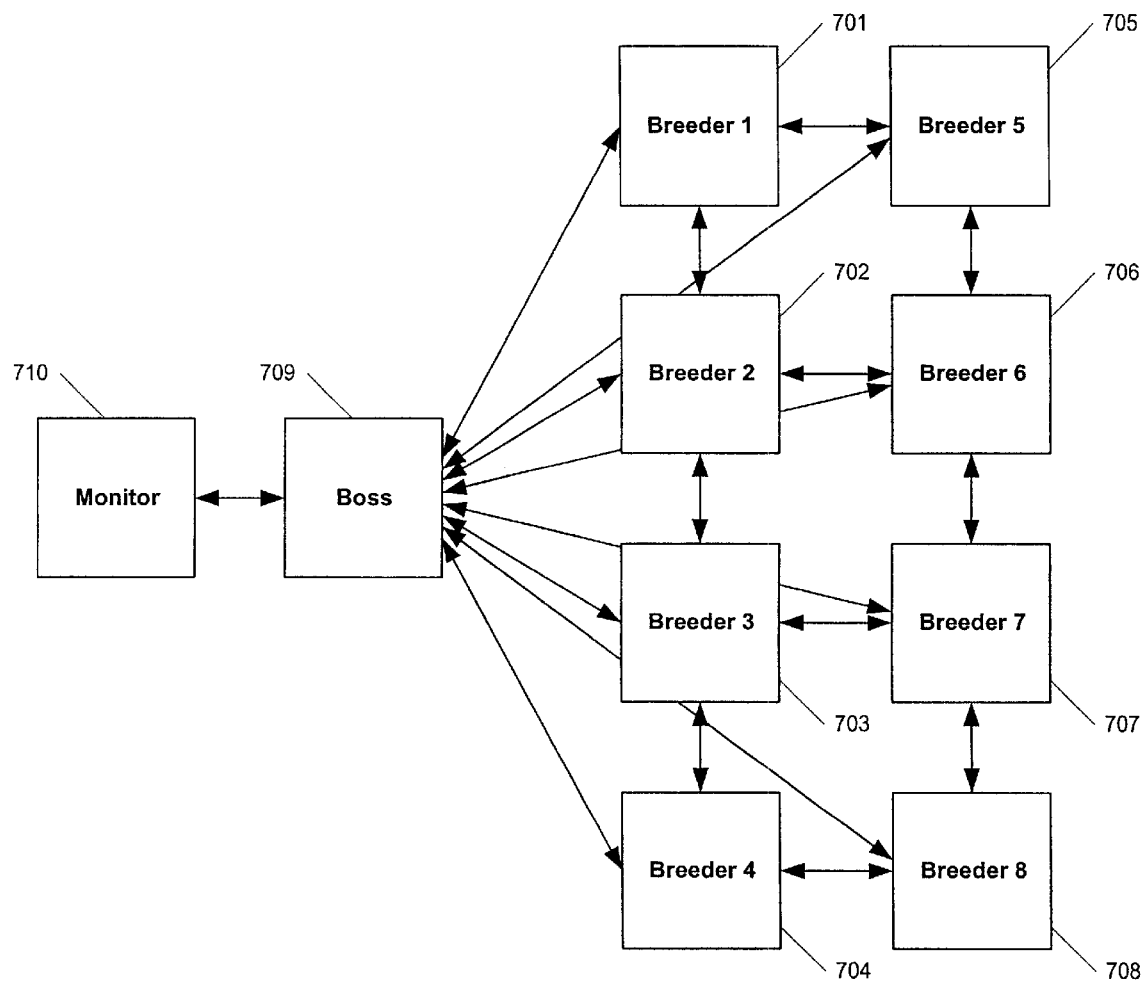
FIG. 7 is a schematic diagram showing communication among the software processes of the invention.

FIG. 7 is a schematic diagram showing communication among the software processes of the invention. The software architecture comprises multiple communicating processes as shown in FIG. 7. Each of the 8 workstations (601–608) runs a Breeder process (701–708) which performs the distributed genetic algorithm (discussed below). The server (609) runs a Boss process (709) which manages all of the Breeders (701–708). Specifically, the Boss (709) assigns each Breeder a set of neighboring Breeders with whom data will be exchanged. The server (609) also runs a Monitor process (710) which displays and records information.

To begin the process of the present invention, the user boots the parallel computer system and runs a script on the server which starts all of the processes. The user then issues a "start run" command to the Boss process which specifies a file containing all of the input parameters. The Boss process then sends a "start run" message to all of the Breeder processes which contains the input parameters.

Upon receiving a "start run" message from the Boss process, each Breeder process begins running the so-called distributed genetic algorithm. The distributed genetic algorithm is an extension of the iterative process detailed in FIG. 5. In the distributed genetic algorithm, each Breeder contains its own deme (subpopulation) and carries out steps of population creation, the population evaluation, and performing of genetic operations as before.

After the genetic operations are performed on each Breeder, a certain number of migrant individuals are selected on the basis of fitness and removed from the local deme. (The number of migrant individuals is specified by an additional input parameter, "migration percentage.") The migrant individuals are sent over the network to neighboring Breeders. The migrant individuals are buffered by the neighboring Breeders, and are assimilated into their destination demes after each neighbor Breeder sends out its own migrant individuals.

The amount of computer time required to evaluate individuals in genetic programming usually varies considerably among demes. Therefore, no attempt is made to synchronize the activities of the algorithm at the various Breeders, since this would require slowing every Breeder to the speed of the slowest. After a few generations, the various Breeders of the system will typically be working on different generations.

After sending migrant individuals, each Breeder gathers statistics about the current generation and selects a best-of-generation individual, then sends this data in an "end-of-generation" message to the Boss process. The Boss process receives the end-of-generation message and passes it immediately to the monitor process. The Monitor process receives the end-of-generation message, displays some data on the server video display, and records the message in a file on the server hard disk.

This process continues until the termination criteria are met. Alternatively, the user may manually stop the run by issuing a "stop run" command to the Boss. The run will also stop in the error case when all of the computers have crashed.

While the foregoing is directed to the preferred embodiment of the present invention, other and further embodiments of the invention may be devised without departing from the basic scope thereof, and the scope thereof is determined by the claims that follow.

What is claimed is:

1. A method for designing a synthesis route for a target molecule, comprising:
    generating a plurality of individuals, wherein each individual encodes a synthesis route;
    decoding each individual to produce a synthesis route comprising at least one reactant molecule and at least one reaction, and
    determining whether the synthesis route satisfies a design goal.

2. The method of claim 1, wherein the individual encodes a synthesis route as a program comprising a plurality of instructions which are executed to produce the synthesis route.

3. The method of claim 2, wherein the program conforms to a constrained structure.

4. The method of claim 1, wherein the decoding step comprises retrieving at least one reactant molecule from a data structure of molecules.

5. The method of claim 4, wherein the decoding step further comprises retrieving at least one set of reaction conditions from a data structure of reaction conditions.

6. The method of claim 5, wherein the decoding step further comprises evaluating at least one reaction utilizing the at least one reactant molecule and the at least one set of reaction conditions to output at least one product molecule.

7. The method of claim 6, wherein the evaluation is performed utilizing a computer-based reaction predictor.

8. The method of claim 6, wherein the evaluation is accomplished by physically performing the reaction.

9. The method of claim 1, wherein the step of determining whether the synthesis route satisfies a design goal comprises determining a structural similarity between a target molecule and a final product molecule of the synthesis route.

10. The method of claim 9, wherein the step of determining structural similarity comprises comparing the final product molecule and the target molecule utilizing a graph isomorphism algorithm.

11. The method of claim 9, wherein the step of determining structural similarity comprises generating and comparing reduced representations of the final product molecule and the target molecule.

12. The method of claim 11, wherein the reduced representation comprises a bit string and wherein the step of comparing reduced representations utilizes a bit string distance metric.

13. The method of claim 1, wherein the step of determining whether the synthesis route satisfies a design goal comprises determining a yield value of the final product molecule.

14. The method of claim 1, further comprising:
    performing a selected operation on at least one selected individual to produce a new individual; and
    adding the individual produced by the selected operation to the population.

15. The method of claim 14, wherein the step of performing a selected operation comprises performing a crossover operation, the crossover operation comprising:
    combining at least one portion from the selected individual and at least one portion from another selected individual to produce a new individual.

16. The method of claim 14, wherein the step of performing a selected operation comprises performing a mutation operation, the mutation operation comprising:
    replacing at least one portion of the selected individual with a randomly generated portion to produce a new individual.

17. The method of claim 14, wherein the step of performing a selected operation comprises performing a molecule noise operation comprising:
    generating a similarity value;
    selecting at least one molecule encoded by the selected individual; and
    modifying the selected individual to encode a new molecule based on the similarity value the selected at least one molecule.

18. The method of claim 14, wherein the selected individual is selected based on the determination of how well the synthesis route associated with the individual satisfies the design goal.

19. The method of claim 14, wherein the selected operation is probabilistically chosen from the group of operations consisting of crossover, mutation, molecule noise and copy.

20. The method of claim 1, wherein the steps are performed utilizing a computer system having a plurality of processors.

21. A computer readable medium containing instructions to perform a method comprising:
    generating a plurality of individuals, wherein each individual encodes a synthesis route;
    decoding each individual to produce a synthesis route comprising at least one reactant molecule and at least one reaction, and
    determining whether the synthesis route satisfies a design goal.

22. The computer readable medium of claim 21, wherein the decoding step comprises:
    retrieving at least one reactant molecule from a data structure of molecules;
    retrieving at least one set of reaction conditions from a data structure of reaction conditions; and
    evaluating at least one reaction utilizing the at least one reactant molecule and the at least one set of reaction conditions to output at least one product molecule.

23. The computer readable medium of claim 22, wherein the evaluation is performed utilizing a computer-based reaction predictor.

24. The computer readable medium of claim 21, wherein the step of determining whether the synthesis route satisfies a design goal comprises determining a structural similarity between a target molecule and a final product molecule of the synthesis route.

25. The computer readable medium of claim 24, wherein the step of determining structural similarity comprises comparing the final product molecule and the target molecule utilizing a graph isomorphism algorithm.

26. The computer readable medium of claim 24, wherein the step of determining structural similarity comprises generating and comparing reduced representations of the final product molecule and the target molecule.

27. The computer readable medium of claim 21, wherein the step of determining whether the synthesis route satisfies a design goal comprises determining a yield value of the final product molecule.

28. The computer readable medium of claim 21, wherein the method further comprises:

performing a selected operation on at least one selected individual to produce a new individual; and adding the individual produced by the selected operation to the population.

29. The computer readable medium of claim 21, wherein the selected operation is probabilistically chosen from the group of operations consisting of crossover, mutation, molecule noise and copy.

30. A parallel computer system to execute instructions to perform a method for designing a synthesis route comprising the steps of:

generating a plurality of individuals, wherein each individual encodes a synthesis route;

decoding each individual to produce a synthesis route comprising at least one reactant molecule and at least one reaction, and determining how well the synthesis route satisfies a design goal.

31. The apparatus of claim 30, wherein the decoding step comprises:

retrieving at least one reactant molecule from a data structure of molecules;

retrieving at least one set of reaction conditions from a data structure of reaction conditions; and evaluating at least one reaction utilizing the at least one reactant molecule and the at least one set of reaction conditions to output at least one product molecule.

32. The apparatus of claim 30, wherein the evaluation is performed utilizing a computer-based reaction predictor.

33. The apparatus of claim 30, wherein the step of determining whether the synthesis route satisfies a design goal comprises determining a structural similarity between a target molecule and a final product molecule of the synthesis route.

34. The apparatus of claim 30, wherein the step of determining structural similarity comprises comparing the final product molecule and the target molecule utilizing a graph isomorphism algorithm.

35. The apparatus of claim 30, wherein the step of determining structural similarity comprises generating and comparing reduced representations of the final product molecule and the target molecule.

36. The apparatus of claim 30, wherein the step of determining whether the synthesis route satisfies a design goal comprises determining a yield value of the final product molecule.

37. The apparatus of claim 30, wherein the method further comprises:

performing a selected operation on at least one selected individual to produce a new individual; and adding the individual produced by the selected operation to the population.

38. The apparatus of claim 30, wherein the selected operation is probabilistically chosen from the group of operations consisting of crossover, mutation, molecule noise and copy.

* * * * *